United States Patent [19]
Amidon et al.

[11] Patent Number: 5,834,022
[45] Date of Patent: Nov. 10, 1998

[54] WATER SOLUBLE PHARMACEUTICAL COATING AND METHOD FOR PRODUCING COATED PHARMACEUTICALS

[75] Inventors: Gordon L. Amidon; John R. Crison, both of Ann Arbor, Mich.

[73] Assignee: Port Systems L.L.C., Ann Arbor, Mich.

[21] Appl. No.: 790,570

[22] Filed: Jan. 29, 1997

Related U.S. Application Data

[62] Division of Ser. No. 594,814, Jan. 31, 1996, Pat. No. 5,686,133.
[51] Int. Cl.$^6$ .............................. A61K 9/14; A61K 9/16
[52] U.S. Cl. ...................... 424/492; 424/490; 424/498; 424/456; 424/478; 427/398.4; 427/2.22; 427/2.14; 427/2.12; 427/355
[58] Field of Search ..................................... 424/451, 456, 424/464, 465, 474, 478, 489–492, 498; 427/2.22, 2.14, 212, 355, 398.4

[56] References Cited

U.S. PATENT DOCUMENTS

| | | | |
|---|---|---|---|
| 4,072,551 | 2/1978 | Dabal et al. | 156/378 |
| 4,540,602 | 9/1985 | Motoyama et al. | 427/213 |
| 4,729,897 | 3/1988 | Poppe et al. | 426/96 |
| 4,769,236 | 9/1988 | Panoz et al. | 424/80 |
| 4,778,676 | 10/1988 | Yang et al. | 424/79 |
| 4,816,177 | 3/1989 | Nelson et al. | 252/181 |
| 4,837,031 | 6/1989 | Denton | 424/464 |
| 4,882,160 | 11/1989 | Yang et al. | 424/440 |
| 5,026,555 | 6/1991 | Killeen | 424/439 |
| 5,275,821 | 1/1994 | Torosian | 424/456 |
| 5,354,560 | 10/1994 | Lovrecich | 424/489 |
| 5,387,421 | 2/1995 | Amidon et al. | 424/472 |
| 5,399,357 | 3/1995 | Akiyama et al. | 424/457 |

OTHER PUBLICATIONS

Abdallah and Mayersohn, "The Preparation and Evaluation of a Tablet Dosage Form of Cyclosporine in Dogs", *Pharm. Res.*, 8:518–522 (1991).

Amidon et al., "A Theoretical Basis for a Biopharmaceutic Drug Classification: The Correlation of In Vitro Drug Product Dissolution and In Vivo Bioavailability", *Pharm. Res.*, 12:413–420 (1995).

Avis, "Remington'S Pharmaceutical Sciences", *Parenteral Preparations*, Mack Publishing Company 15th edition, pp. 1483–1485 (1975).

Bowers, "Cyclosporin Analysis by High–Performance Liquid Chromatography: Precision, Accuracy, and Minimum Detectable Quantity" 22:115 1154 (1990).

Crison, Estimating the Dissolution and Absorption of Water Insoluble Drugs In The Small Intestine, Ph.D. Thesis, The University of Michigan (1993).

Crison and Amidon, "Expected Variation In Bioavailability for Water Insoluble Drugs", *Bio–International 2, Bioavailability Bioequivalence and Pharmacokinetic Studies*, Blume and Midha Editors, (1995).

Dressman and Fleisher, Mixing–Tank Model for Predicting Dissolution Rate Control of Oral Absorption, *J. Pharm. Sci.*, 75:109–116 (1986).

Grant and Higuchi, "Solubility Behavior of Organic Compounds", *Techniques of Chemistry*, vol. 21, W.H. Saunders, Editor, John Wiley & Sons, Toronto, Canada, pp. 474–486 (1990).

(List continued on next page.)

Primary Examiner—Gollemudi S. Kishore
Attorney, Agent, or Firm—Kohn & Associates

[57] ABSTRACT

A method of making a pharmaceutical composition is disclosed. The method includes the steps of contacting at least one pharmaceutical ingredient with a mixture consisting essentially of gelatin and lecithin to increase the dissolution rate of water-insoluble pharmaceutical ingredients. A pharmaceutical excipient coating for increasing the dissolution rate of water-insoluble pharmaceutical ingredients is also disclosed. The coating consists essentially of gelatin and lecithin.

5 Claims, 5 Drawing Sheets

OTHER PUBLICATIONS

Jones, "Fluidized Bed Processing and Drying" *Int. Soc. of Pharm. Eng.* pp. 1–7 (1991).

Katchen and Symchowicz, "Correlation of Dissolution Rate and Griseofulvin Absorption in Man", *J. Pharm. Sci.*, 56:1108–1110 (1967).

Merck Index, Eleventh Edition, Merck & Co., Inc., Rahway, N.J. (1989).

Oh et al., Estimating the Fraction Dose Absorbed from Suspensions of Poorly Soluble Compounds in Humans: A Mathematical Model, *Pharmaceutical Research*, 10:264–270 (1993).

Reymond et al., "On The Dose Dependency of Cyclosporin A Absorption and Disposition in Healthy Volunteers", *J. Pharmacokinetetic and Biopharmaceutics*, 16:331–353 )1988).

Swanson et al., Nifedipine Gastrointestinal Therapeutic System, *Amer. J. of Med.*, 83:3–9 (1987).

WATER SOLUBLE PHARMACEUTICAL COATING AND METHOD FOR PRODUCING COATED PHARMACEUTICALS

This application is a division of Ser. No. 08/594,814 filed Jan. 31, 1996, now U.S. Pat. No. 5,686,133.

TECHNICAL FIELD

The present invention generally relates to a pharmaceutical excipient coating. More particularly, the present invention relates to a pharmaceutical excipient coating and method of making pharmaceutical compositions.

BACKGROUND OF THE INVENTION

It is well known in the art that there are solid drugs which are scarcely soluble in water. Due to their low solubilities, these drugs have a correspondingly low degree of bioavailability.

Several prior art processes have been developed in efforts to increase the solubility and, hence, the bioavailability of poorly soluble pharmaceuticals or drugs. One such prior art process discloses the use of water-soluble high-molecular weight substances having low melting points, such as Carbowax, in combination with an insoluble drug. However, compositions prepared by this process possess poor redispersibility in water due to the low melting point and, therefore, are undesirable as pharmaceutical excipients.

Other methods of increasing the aqueous dissolution rate of poorly water-soluble drugs include the use of organic solvents to solubilize the poorly water-soluble drug or pharmaceutical composition. One such method is disclosed in U.S. Pat. No. 4,540,602 to Motoyama et al., issued Sep. 10, 1985, which discloses a process for the preparation of activated pharmaceutical compositions containing a solid drug that is scarcely soluble in water. The method includes the steps of dissolving or solubilizing a solid drug, that is highly insoluble in water, in a low-boiling point hydrophobic organic solvent such as lecithin. The solubilized drug is then emulsified in the presence of a water-soluble, high-molecular weight substance, such as gelatin, and the drug is removed from the emulsion.

The method disclosed in the Motoyama et al. reference solubilizes the drug and then resolidifies/recrystalizes the drug in a water-soluble matrix such as gelatin or lecithin. The Motoyama et al. method requires the use of organic solvents in order to solubilize the drug. This method has several inherent disadvantages or drawbacks. First, since the drug is solubilized and then recrystalized, the recrystalized product must be reidentified since polymorphic changes can occur when the drug is recrystalized in a different solvent than the solvent originally used. Additionally, since the compounds of interest in the Motoyama patent are water-insoluble, organic solvents must be used in order to solubilize the drugs of interest. The use of organic solvents creates further problems with the health and safety aspects of organic solvents and the environmental unfriendliness and safety of organic solvents. All of these factors associated with the use of organic solvents considerably add to the cost of utilizing organic solvents in a method to increase the solubility of water-insoluble drugs as organic solvent recovery and containment devices are very costly. Other known surface active excipients can be affected by gastric pH or can be destructive to the intestinal mucosa.

Therefore, it would be advantageous and desirable to have a method of increasing the dissolution rate of poorly water-soluble pharmaceuticals which avoids the drawbacks of the prior art methods. Furthermore, it would be desirable to have a method which is completely aqueous-based in order to avoid the necessity for recharacterization of the pharmaceuticals or drugs according to the solubilization method disclosed above and also eliminating the cost and both health and environmental safety aspects of using organic solvents. It would be a further advantage to have a coating and method of coating a drug which is not affected by gastric pH, can be applied to a drug in aqueous solution using standard manufacturing and equipment for coating the drug, and which is safe and not destructive to the intestinal mucosa.

By combining the method and coating of the present invention with poorly water-soluble drugs or pharmaceutical compositions, optimal advantage can be taken of the potential potency and efficacy of poorly water-soluble drugs by increasing their bioavailability. The present invention provides an improved method and coating for providing poorly water-soluble drugs with a means for a greater dissolution rate and, hence, greater bioavailability which includes all of the aforementioned mentioned advantages.

SUMMARY OF THE INVENTION AND ADVANTAGES

In accordance with the present invention, there is provided a method of making a pharmaceutical composition by contacting at least one pharmaceutical ingredient with a mixture consisting essentially of gelatin and lecithin to increase the dissolution rate of water-insoluble pharmaceutical ingredients.

The present invention further provides a pharmaceutical excipient coating for increasing the dissolution rate of water-insoluble pharmaceutical ingredient wherein the coating consists essentially of gelatin and lecithin.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
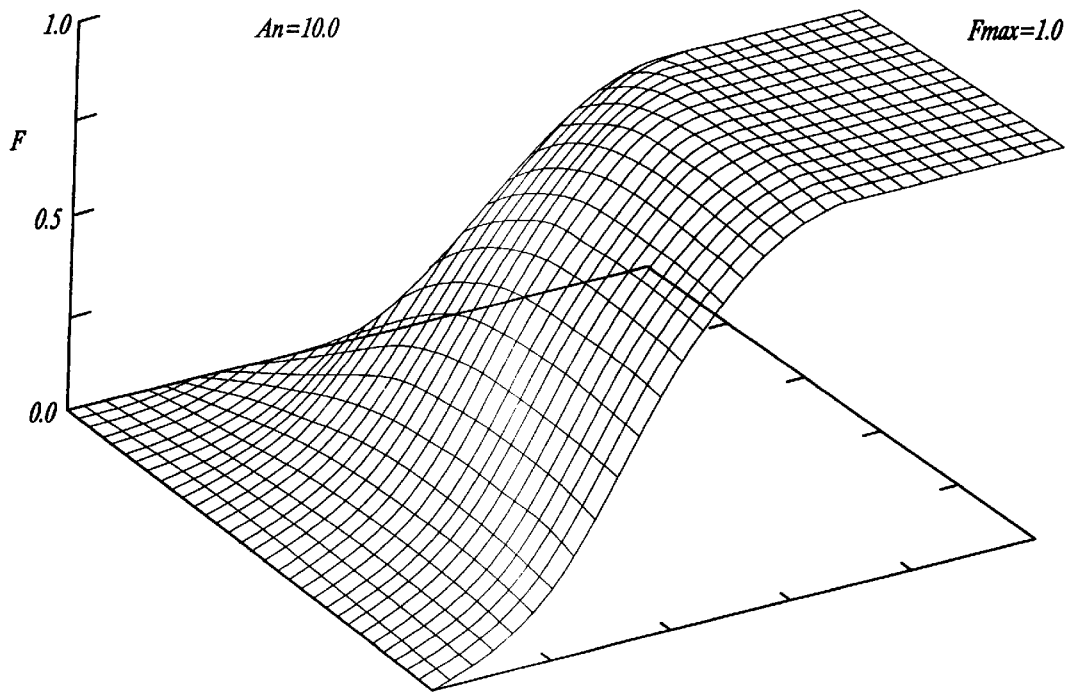
FIG. 1a is a plot of the fraction dose absorbed vs. dose and dissolution number, i.e., the dose of drug given and the dissolution rate in a dimensionless format.

A method of making a pharmaceutical composition having increased dissolution rate of water-insoluble pharmaceutical ingredients is disclosed. The method generally includes the steps of contacting at least one pharmaceutical ingredient with a mixture including gelatin and lecithin.

More than one pharmaceutical ingredient at a time can be treated according to the present invention to yield a desired pharmaceutical composition. Additionally, poorly-water-soluble pharmaceutical ingredients can be treated according to the present invention and can then be used in combination with other pharmaceutical ingredients which therefore may or may not be poorly water-soluble.

The term "pharmaceutical ingredient" includes any pharmaceutical compound, drug, or composition in solid form such as powder or granules.

The method includes the steps of dissolving gelatin in water heated to between 35°–40° C. Lecithin is added to the gelatin/water mixture and is thoroughly mixed therein. At least one pharmaceutical ingredient in solid particulate form is then added slowly and mixed so as to cause thorough and uniform coating of the particles of the pharmaceutical ingredient. Following coating with the gelatin/lecithin mixture, the coated pharmaceutical ingredient is then dried.

Referring to Table 1, the general range of concentrations of excipient (i.e., the lecithin/gelatin) and pharmaceutical ingredient is shown. The concentration in the coating solution of gelatin and lecithin broadly ranges from approximately 0.001–99.9% (w/v) each and more preferably 0.01% to 2.0% each. The concentration in the coating solution of the pharmaceutical ingredient ranges from approximately 0.1–15.0% (w/v). It is preferable that the lecithin and gelatin be present in a 1:1 ratio.

The contacting step includes coating the pharmaceutical ingredient with the mixture including water gelatin and lecithin. The coating step can be accomplished by simple immersion of the particles of the pharmaceutical ingredient. It is believed that the gelatin coats the particles of the pharmaceutical ingredient and prevents aggregation or clumping of the particles. The lecithin element is thought to reduce surface tension thereby preventing aggregation or form a microemulsion or to form micelles which facilitate dissolution of the pharmaceutical ingredient. In acting in this complementary fashion, the coating including gelatin and lecithin increases the dissolution rate of water-insoluble pharmaceutical ingredients. The above-described theory is provided merely for descriptive purposes and is no way intended to limit the scope of the present invention.

After the pharmaceutical ingredient(s) is coated with the aqueous mixture of gelatin and lecithin, the aqueous solvent water can be removed by various techniques.

The solvent removal or drying of the coated pharmaceutical ingredient can be accomplished by lyophylization or freeze drying of the coated particles by techniques known to those skilled in the art. Lyophylization, or freeze-drying, is a process by which a solid is dissolved or suspended in a liquid, frozen and the water is sublimed from the product after it is frozen. The advantage of this process is that the stability of biologicals and pharmaceuticals that are unstable in the presence of water can be increased without elevated temperatures that often occur during processing. [Avis, 1975].

The coated pharmaceutical ingredient can also be dried by the method known in the art as spray drying. Spray drying and fluidized bed processing are widely used in the industry for drying, granulating and coating active ingredients (drugs) [Jones, 1991]. These methods enable the pharmaceutical formulator to convert solid drug particles into powders and granulations with excellent flow and compression properties for high speed manufacturing of tablets and capsules. The basic design consists of a spray nozzle, a drying chamber, and an air source. The drug, along with other solubilized or suspended materials are pumped through a spray nozzle, atomized and dried into a fine, amorphous powder. Alternatively, it is coated onto sugar seeds (non-pareils) or dried into aggregates. The spraying rate,. air flow and temperature of the drying chamber all can be varied to produce the desired end product. This process is widely used in the pharmaceutical industry and the invention described in this patent has been shown to be manufacturable by this method.

The coated pharmaceutical ingredient can also by granulated to obtain granules having good redispersability in water with granule diameters in the range of 4 to 1000 microns. The granulation can be accomplished using a fluid bed granulator (Glatt® Ramsey, N.J.) using means well known to those skilled in the art.

Additionally, the method of the present invention can include the step of spray coating the gelatin/lecithin coated pharmaceutical ingredient onto micronized particles. Micronization is the process by which solid drug particles are reduced in size. Since the dissolution rate is directly proportional to the surface area of the solid, and reducing the particle size increases the surface area, reducing the particle size increases the dissolution rate. The theoretical basis for using micronization to increase the dissolution rate is as follows:

Drug dissolution is defined by equation 1;

$$\frac{dm}{dt} = \frac{SA \cdot D}{h} \cdot (C_s - C_b) \tag{1}$$

where m is the mass of drug, t is time, SA is surface area, $C_s$ is the solubility of the drug, h is the diffusional boundary layer thickness, and $C_b$ is the concentration of drug in the bulk solution. Applying equation 1 to a spherical particle and assuming sink conditions;

$$\frac{dr}{dt} = \frac{D}{h\rho} \cdot C_s \tag{2}$$

Furthermore, if we integrate equation 2 and assume the diffusional boundary layer to be equal to the radius of the particle, then the mass of drug dissolved for a given period of time is inversely proportional to the square of the radius of the particle.

$$\int_{r_0}^{r} r \, dr = \frac{D \cdot C_s}{h\rho} \int_{0}^{t} dt$$

-continued $$r - r_0 = \frac{D \cdot C_s}{h\rho} t$$

$$M_0^{1/3} - M^{1/3} = \frac{M_0^{1/3}}{2r} \cdot \frac{2D \cdot C_s}{r\rho} t$$

$$\%D = \left(1 - \frac{D \cdot C_s}{r^2 \rho} t\right)^2$$

where % D is the percent of drug dissolved.

Micronizing equipment typically create particles with diameters in the micron range (1 to 20 μm). However, there are drawbacks to micronizing water insoluble drugs. Since most water insoluble drugs have very high surface energy, as the surface area increases, so does the surface energy and micronized particles generally aggregate to reduce the amount of free energy resulting in particles larger that prior to micronization (see figure below). For example;

$$\Delta G = \gamma \cdot SA = \gamma \cdot \pi r^2$$

where ΔG is the free energy, γ is the surface tension of the solid and r is the particle radius. Surface active materials, such as in the invention presented here, reduce the surface tension of the solid, lower the free energy of the system and eliminate particle aggregation. Examples of commercially available micronizers are Fluid Energy Aljet (Plumsteadville, Pa.) and Sturtevant, Inc. (Boston, Mass.).

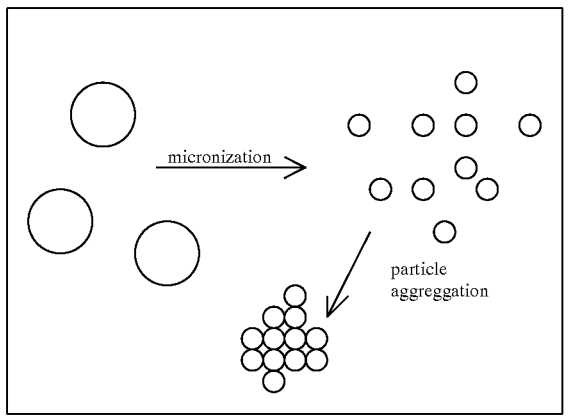

Although micronization results in increased surface area causing particle aggregation, which can negate the benefit of micronization and is an expensive manufacturing step, it does have the significant benefit of increasing the dissolution rate of water insoluble drugs if particle aggregation can be prevented.

The active pharmaceutical ingredient utilized in the method of the present invention can include griseofulvin, cyclosporin (see Table 3 for aqueous solubilities of these compounds and other suitable pharmaceutical ingredients or drugs having low water solubility).

Other examples of water insoluble drugs than can benefit from the present invention are listed in Table 3. This list in Table 3 is not meant to be exhaustive, but rather as an exemplary list.

Applicant has conducted dissolution/bioavailability studies demonstrating the increased dissolution rate of water-insoluble pharmaceutical ingredients according to the present invention.

Figure 2:
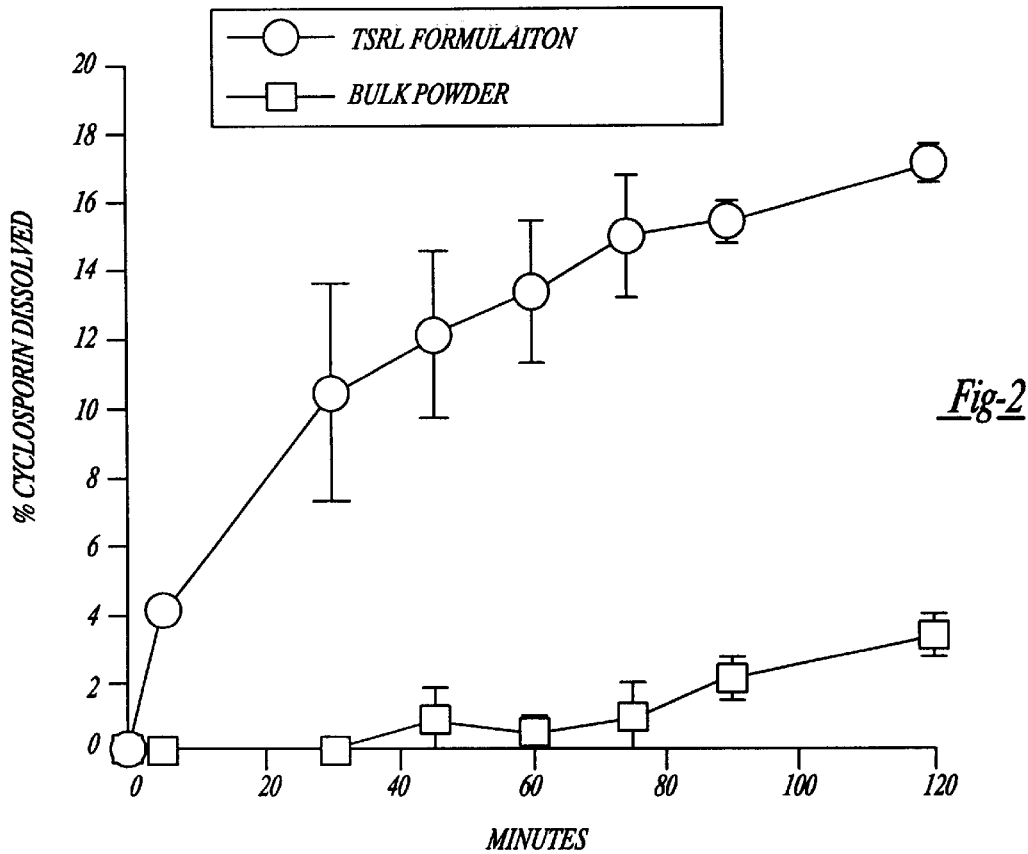
FIG. 2 is a graph showing the dissolution profiles of bulk cyclosporin powder and bulk cyclosporin coated with the lecithin/gelatin coating according to the present invention in 0.01% sodium lauryl sulfate (SLS)

Referring to FIG. 2, initial dissolution rates for cyclosporin formulations are shown. The dissolution rate for cyclosporin coated with lecithin/gelatin was shown to be greater than for bulk cyclosporin powder.

Figure 4:
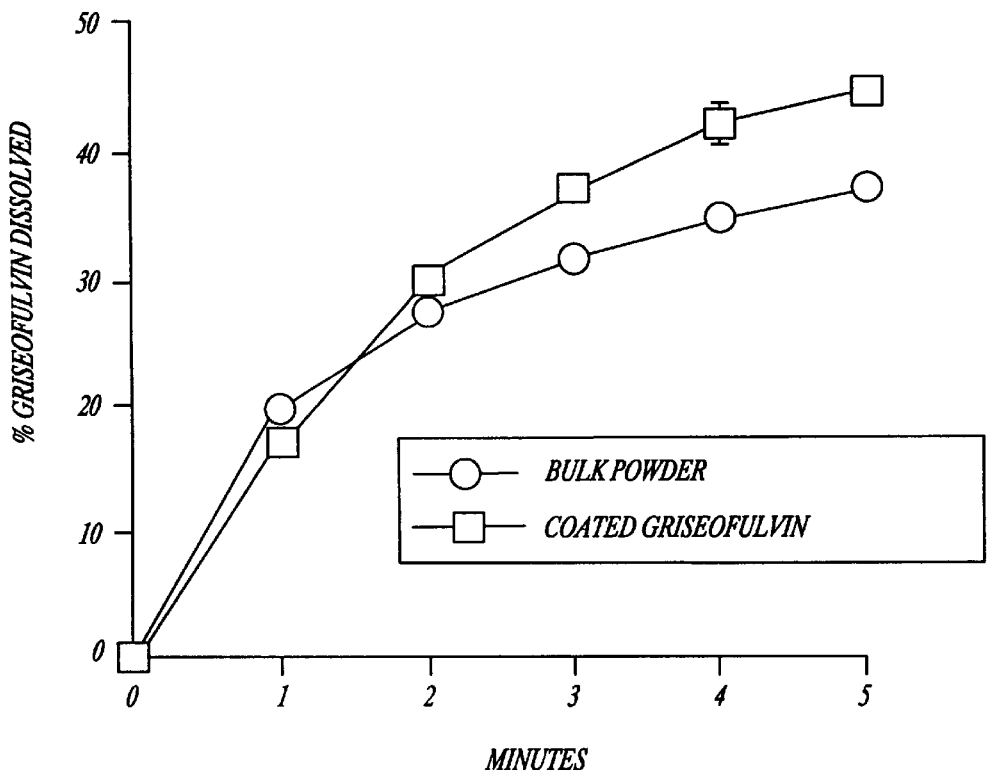
FIG. 4 is a graph showing the dissolution profile of coated and uncoated griseofulvin dissolved in 0.25% SLS @ 37° C.

Referring to FIGS. 2 and 4, the results of studies performed in order to ascertain the percentage of either cyclosporin or griseofulvin dissolved in either a 0.01% solution of sodium lauryl sulfate (for cyclosporin) or 0.25% sodium lauryl sulfate (for griseofulvin) are shown. The results of the dissolution studies shown in FIGS. 2 and 4 illustrate that both the initial dissolution rates and the total dissolution rates over time were greater for both cyclosporin and griseofulvin treated with the lecithin/gelatin coating of the present invention than with the non-coated formulations tested. The results illustrate for both cyclosporin and griseofulvin that the initial rates of dissolution and the dissolution over time were both faster and greater when each compound was treated with the lecithin/gelatin coating. Additionally, the results shown in these Figures demonstrate that cyclosporin treated with the lecithin/gelatin coating of the present invention had both a greater initial dissolution rate and a greater dissolution rate over time than bulk cyclosporin powder. The same results were true for the griseofulvin treated with the lecithin/gelatin coating of the present invention, that is, the griseofulvin treated with the lecithin/gelatin coating demonstrated both a greater initial dissolution rate and a greater overall percentage of dissolution over time as compared to untreated bulk griseofulvin powder.

Referring to Table 2, area under the curve (AUC) results of plasma concentration-time curves for cyclosporin formulations are illustrated. Table 2 illustrates a doubling of the relative bioavailability of cyclosporin given orally in dogs for lecithin/gelatin coated cyclosporin versus bulk cyclosporin powder.

Theoretical considerations of drug dissolution and absorption in the human gastrointestinal tract indicate that for water insoluble drugs two independent variables will control drug absorption: the dissolution rate extent of dissolution and dose of drug given. The significance of this analysis is that for water insoluble drugs, the fraction dose absorbed is inversely proportional to dose and is directly proportion to the dissolution rate. Therefore, in vivo solubilization and dissolution are important determinants of drug absorption.

Intestinal Drug Absorption—Theoretical Considerations

Membrane Permeability and Luminal/Wall Concentration

The fundamental equation describing drug absorption is;

$$J_w = P_w \cdot C_w \qquad \text{equation 1}$$

where, $J_w(x,y,z,t)$ is the drug flux (mass/time/area) through the intestinal wall at any position and time, $P_w(x,y,x,t)$ is the permeability of this (complex) membrane, and $C_w(x,y,z,t)$ the drug concentration at the membrane (wall) surface (know as Ficks' First Law). This is Ficks' First Law applied to a membrane and applies at each point along the membrane (1) i.e. equation 1 is a local law pertaining to each point along the intestinal membrane. Equation (1) states that the critical parameters governing drug absorption are the intestinal permeability and the concentration of drug in solution at the intestinal surface. $P_w$ here is assumed to be high since the drugs are lipophillic. Therefore the focus will be the term $C_w$.

In Vivo Drug Dissolution and Luminal/Wall Concentration

The equation which describes the processes governing mass transport in the intestine (tube) is (15):

$$\partial C/\partial t + v \cdot \nabla c = D\nabla^2 C + R \quad \text{equation 2}$$

where, C is the local concentration, v is the local velocity, D the diffusivity, and R the rate of production of solute. This equation applies to all components in the intestinal fluid medium and, in general, is much too complex to solve. However, a simpler quantitative and predictive model for drug absorption based on this equation has been developed [Amidon et al., 1995; Crison and Amidon, 1995]. This model considers a segment of intestine over which the permeability may be considered constant, a plug flow fluid with the suspended particles as moving with the fluid, no significant particle-particle interactions (i.e. aggregation) and dissolution in the small particle limit, leading to the following pair of differential equations in dimensionless form; and $$dr^4/dz^* = -(Dn/3)C^4(1-C)/r^4 \quad \text{equation 3}$$

$$dC^4/dz^* = DoDn.r^4(1-C^4) - 2AnC^4 \quad \text{equation 4}$$

where $$z^4 = z/L = (v_z/L)t = t^4$$

$$t^4 = t/(L/v_z) = t/(AL/Q) = t/(V/Q)$$

where L = tube length, $v_z$ = axial fluid velocity in the tube, A = tube surface area, area = $2\pi RL$, R = tube radius, Q = fluid rate = $Av_z$. The three important dimensionless groups are;

$$Do = \text{Dose Number} = \frac{M_o/V_o}{C_s} \quad \text{equation 5}$$

$$Dn = \text{Dissolution Number} = \quad \text{equation 6}$$

$$\frac{DC_s}{r_o} \cdot \frac{4\pi r_o^2}{\frac{4}{3}\pi r_o^3 \rho} \cdot t_{rct} = \frac{3DC_s}{r_o^2 \rho} \cdot t_{ret} = \frac{t_{ret}}{t_{Disc}}$$

$$An = \text{Absorption Number} = \frac{P_{eff}}{R} \cdot t_{res} = t_{abs}^{-1} \cdot t_{res} \quad \text{equation 7}$$

$t_{res} = \pi R^2 L/Q$ = mean tube residence time.

$t_{Disc} = \frac{r_o^2 \rho}{3DC_s}$ = time required for particle of the drug to dissolve.

$t_{abs}^{-1} = k_{abs} = 2 \cdot \frac{P_{eff}}{R}$ = the effective absorption rate constant.

Where, in addition to the symbols defined previously, $M_o$ is the dose, and $r_o$ is the initial particle radius, $C_s$ is the solubility, $\rho$ is the density, $P_{eff}$ is the effective permeability, $t_{res}$ is the residence time, $t_{abs}$ is the absorption time, and $t_{diss}$ is the dissolution time [Oh et al., 1993].

The initial conditions for this set of differential equations, are:

$r = r_o \ t = 0$ $C = C_o \ t = 0$

It is convenient to define a more general initial condition for the concentration of drug entering the intestine using the initial saturation, Is, $C_z(0)$ $C_s$ where $C_s$ is the solubility of the drug, and $C_z(0)$ is the concentration of the drug entering the intestine.

As is evident from the above dimensional analysis of Equation 2, there are three dimensionless groups that describe the total dissolution and absorption process of drugs in the intestine; the dissolution number(DN), dose number(Do), and absorption number(An), or the dissolution rate, the dose of drug given, and the rate of absorption, respectively.

Strategies for Improving the Dissolution and Absorption of Water Insoluble Drugs The class of drugs that are being considered in this patent are those that have low solubility, i.e., drugs where the concentration greatly exceeds the solubility. The absorption of these drugs is limited by how much drug can get into solution. According to the Hixson-Crowell cube root law for estimating the dissolution of a powder, the percent of drug in solution in a given period of time is a function of the particle size and the solubility.

$$\% D = \left[ \frac{DC_s}{r^2 \rho} \cdot t \right]^3 \times 100$$

Where D, $C_s$, r, t and $\rho$ are previously defined. In the case of water insoluble drugs, the solubility, or $C_s$ is low such that the dose of drug given exceeds the amount of fluids available in the GI tract for complete dissolution to take place. Therefore, reducing the particle size or increasing the solubility, or both, are methods for increasing the dissolution rate and absorption of a water insoluble drug.

There are disadvantages to these two methods. First, due to their high lipophillic nature, these drugs have very high surface energy and the interfacial tension between the solid and water is high. The free energy for particles in water is proportional to the interfacial tension and the surface area of the particle as follows;

$$\Delta G = \gamma \ SA$$

Where $\Delta G$ is the free energy of the system, $\gamma$ is the interfacial tension between the liquid and solid, and SA is the surface area of the solid. Reducing the particle size increases the surface area resulting in an increase in the free energy. To lower the free energy, the particles aggregate and negate the utility of particle size reduction.

The second disadvantage comes from attempting to increase the solubility. Two methods can be used to increase the solubility of a drug, 1) formation of a salt, and 2) incorporating surfactants in the formulation. Salt formation has been used successfully but is limited to weak acids and bases. In theory, surfactants should work well to increase the solubility, however the concentration of surfactants needed to overcome the dilution effect of the GI tract often exceeds safe levels. Since surfactants are surface active, effective concentrations can often disrupt biological membranes creating holes in the intestinal mucosa.

Examples of drugs currently on the market that fall into the category of water insoluble drugs are listed in Table 3. The volume of fluid required to achieve complete dissolution in given in column 4. Assuming that a dose of drug is normally administered with a glass of water, approximately 0.25 liters, it is clear that fluid requirements for complete dissolution greatly exceed the fluid initially available. The brevity of this list confirms the importance of a drugs solubility to achieving a successful, marketable product.

Figure 1B:
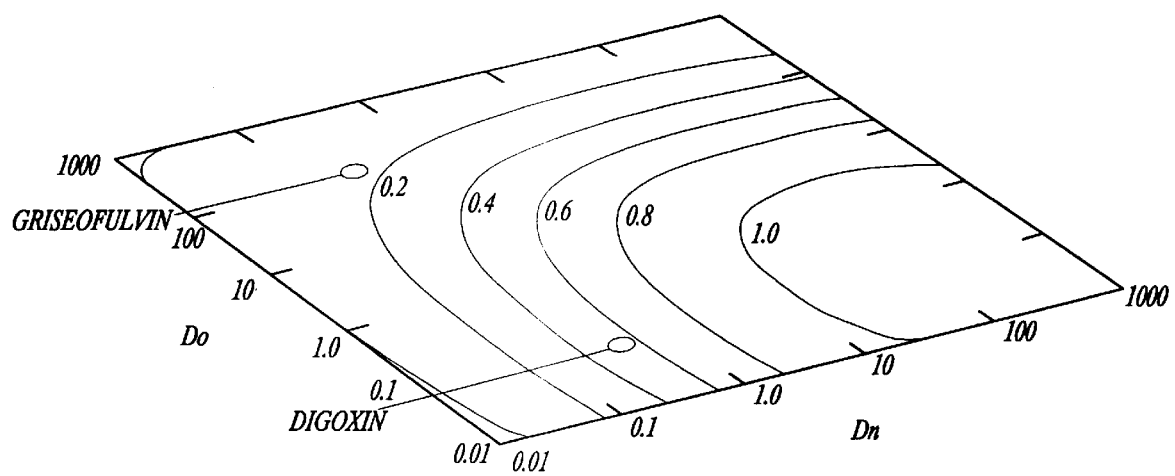
FIG. 1b is a plot of Do vs. DN for griseofulvin and digoxin which are drugs which have similar solubilities (0.017 mg/ml and 0.024 mg/ml, respectively) but have different absorption potentials due to the dose (500 mg vs. 0.5 mg)

The significance of solubility and dissolution rate to absorption are clearly defined in the dose and dissolution numbers. More precisely, the dissolution rate is important due to the limited residence time in the intestine for any given drug particle. The dependency of absorption on dose and dissolution is also noteworthy since it emphasizes that it is the dose number rather than just the solubility, that needs to be included in predicting drug absorption. Other physical constants such as diffusivity and particle density contribute to the dissolution process, however, the range of values for these constants for most organic compounds is small. FIGS. 1a–b are plots of the fraction of dose absorbed vs. dose and dissolution number as generated from equations 2–6. The surface presented in these Figures clearly shows that reduction of particle size is a valid method for increasing the amount of drug absorbed, provided the particles don't aggregate and form large clumps. Below are two examples illustrating this invention.

EXAMPLES

The approach taken by this invention is to coat the drug particles so that; 1) particle aggregation does not occur, and 2) surface energy is lowered so that wetting of the solid in the GI fluids is rapid.

Cyclosporin, an immunosuppressive drug with an aqueous solubility of 0.006 mg/ml at 37° C., was coated with lecithin and gelatin as described above. The lecithin/gelatin formula was prepared by dissolving 1 gm each of gelatin, USP/NF and lecithin NF in 100 ml of water. 0.5 gm of cyclosporin was added to this liquid and mixed on an electric stir plate at room temperature for two hours to coat the particles. The suspension was then placed on a freeze drier and the moisture was removed by lyophylization.

Both the in vitro and in vivo performance of this formulation were tested and compared to the bulk powder of which the formulated material was made from.

IN VITRO PERFORMANCE OF INVENTION

Figure 3:
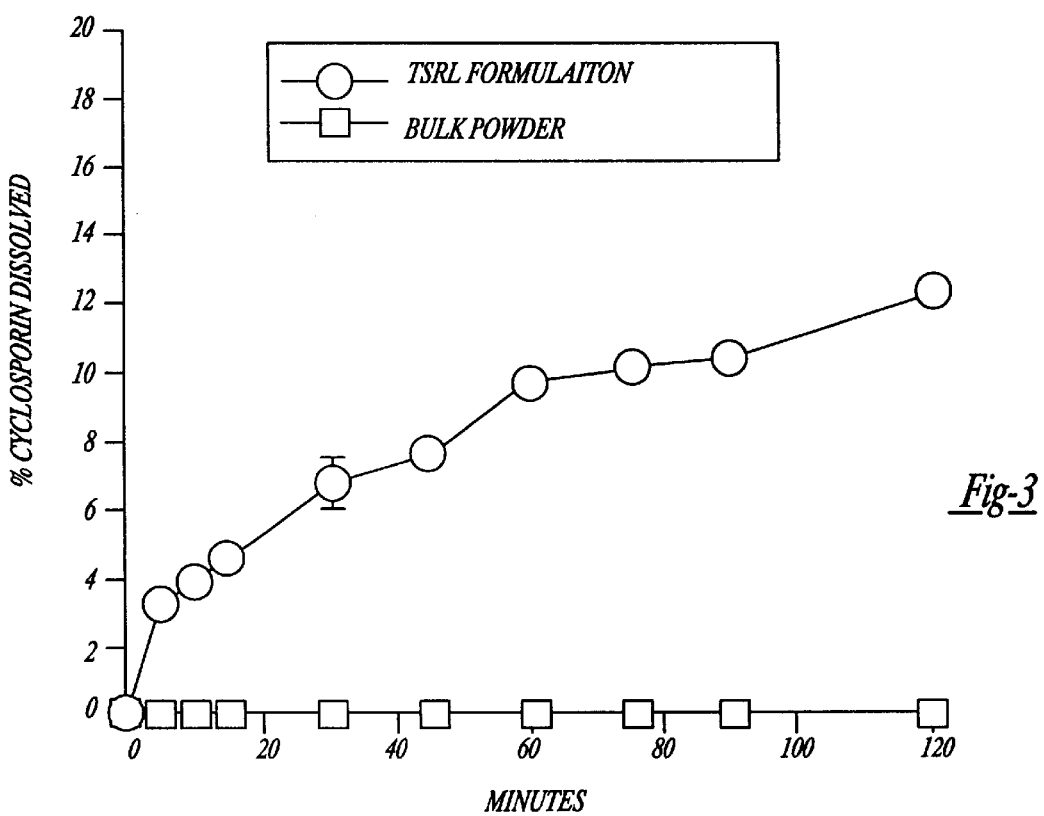
FIG. 3 is a graph showing the percent of bulk cyclosporin powder and bulk cyclosporin powder coated with the lecithin/gelatin coating according to the present invention dissolved in simulated intestinal fluid (SIP) at pH 7.5 @ 37° C.

FIGS. 2 and 3 show the dissolution profile of cyclosporin bulk powder, with and without the lecithin/gelatin coating in 0.01% sodium lauryl sulfate and Simulated Intestinal Fluid, pH 7.5 at 37° C. In the surfactant solution, 17% of the lecithin/gelatin formulation was in solution after 120 minutes compared to the bulk powder which was 3.4% in solution in the same amount of time. In the Simulated Intestinal Fluid, 12% of the coated drug was in solution in 120 minutes compared to 0% (non-detachable) of the bulk powder. The lower levels of dissolved drug in the SIF compared to the surfactant solution may be due to a salting out effect [Grant and Higuchi, 1990].

Griseofulvin is another example of a water insoluble drug that benefits from this invention. FIG. 4 shows the dissolution of griseofulvin in 0.25% SLS at 37° C. After 5 minutes, a 21% increase in amount of griseofulvin in solution was observed using the coating of the present invention.

IN VIVO PERFORMANCE OF THE INVENTION

Figure 5:
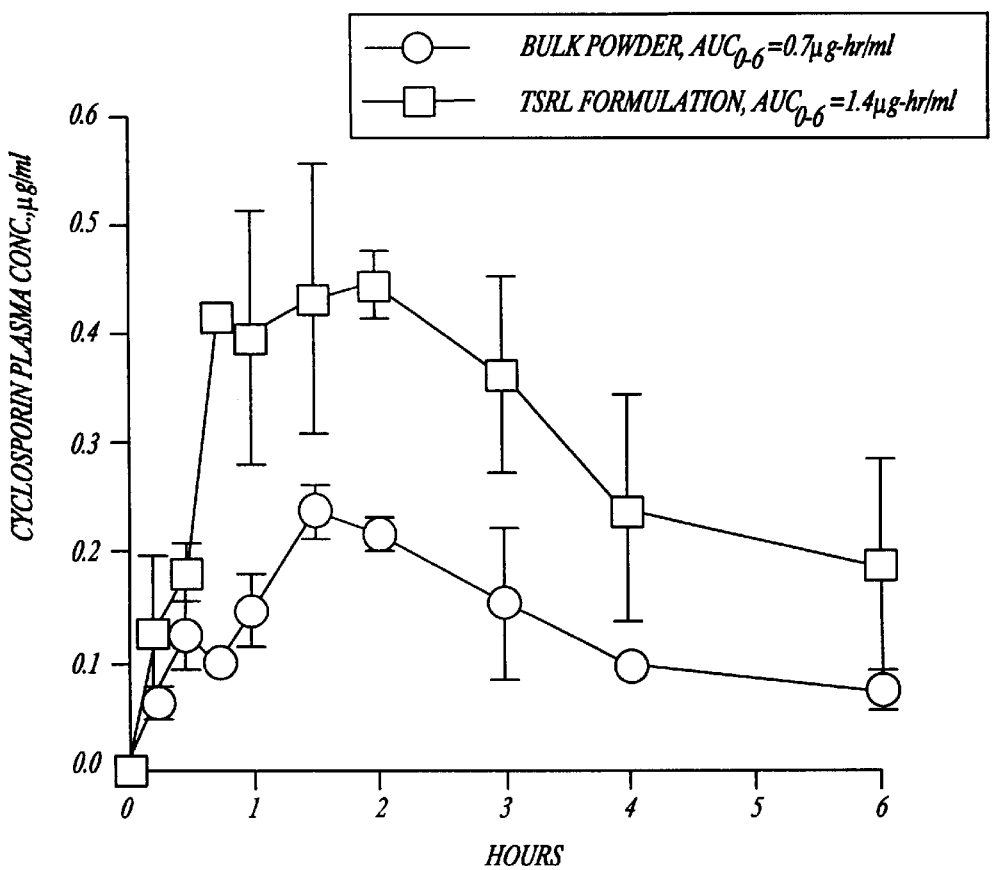
FIG. 5 is a graph showing dog plasma levels of cyclosporin bulk powder and cyclosporin bulk powder formulated with a lecithin/gelatin mixture according to the present invention after oral administration wherein the area under the curve (AUC) for the lecithin/gelatin coated formulation in two (2) times the AUC for the bulk powder.

The same material used in the in vitro experiments was administered to dogs both as the bulk powder and formulated with lecithin and gelatin as described above. The lecithin/gelatin formulation and bulk powder were suspended in 10 ml of water administered via a gastric tube followed by 40 ml of water to rinse out the tube. Plasma samples were taken at 0, 15, 30, 60, 90, 120, 180, 240 and 360 minutes and assayed for cyclosporin content. FIG. 5 shows the results of this study (Abdallah and Mayersohn, 1991; (Bowers, 1990]. Based on these results, the lecithin/gelatin formulation showed a 2.0-fold increase in bioavailability relative to the bulk powder.

FIG. 5 illustrates the results of a study performed to determine the relative plasma concentration of cyclosporin over time following oral administration. The data illustrated in FIG. 6 suggests that coated cyclosporin powder was more readily dissolved into the intestinal lumen than was the same amount of bulk cyclosporin powder.

Figure 8:
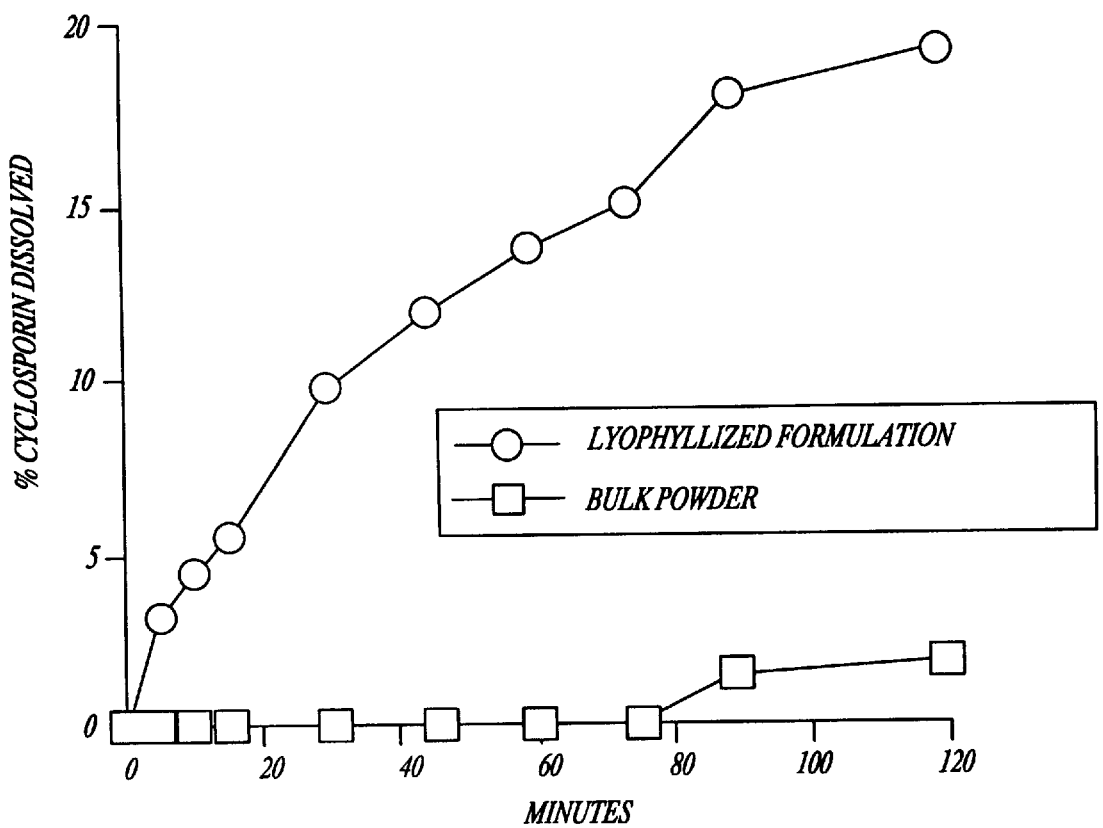
FIG. 8 is a graph showing the dissolution of lyophyllized lecithin/gelatin coated cyclosporin compared with bulk cyclosporin powder; in Milli:-Q water @ 37° C.

As was stated above, the method of the present invention can include the manufacture of pharmaceutical ingredients treated with the lecithin/gelatin coating which is then lyophilized or the pharmaceutical ingredient treated with the lecithin/gelatin coating can be spray coated onto beads. Referring to FIG. 8, lyophilized cyclosporin formulation treated with the lecithin/gelatin coating and bulk cyclosporin powder were compared. The percentage cyclosporin dissolved in Milli-Q (Millipore, Corp.) (deionized, distilled water) over time is illustrated. The lyophilized cyclosporin coated with lecithin/gelatin demonstrated both a greater initial dissolution rate and greater overall percentage dissolution of coated cyclosporin as compared to the bulk cyclosporin powder.

Figure 6:
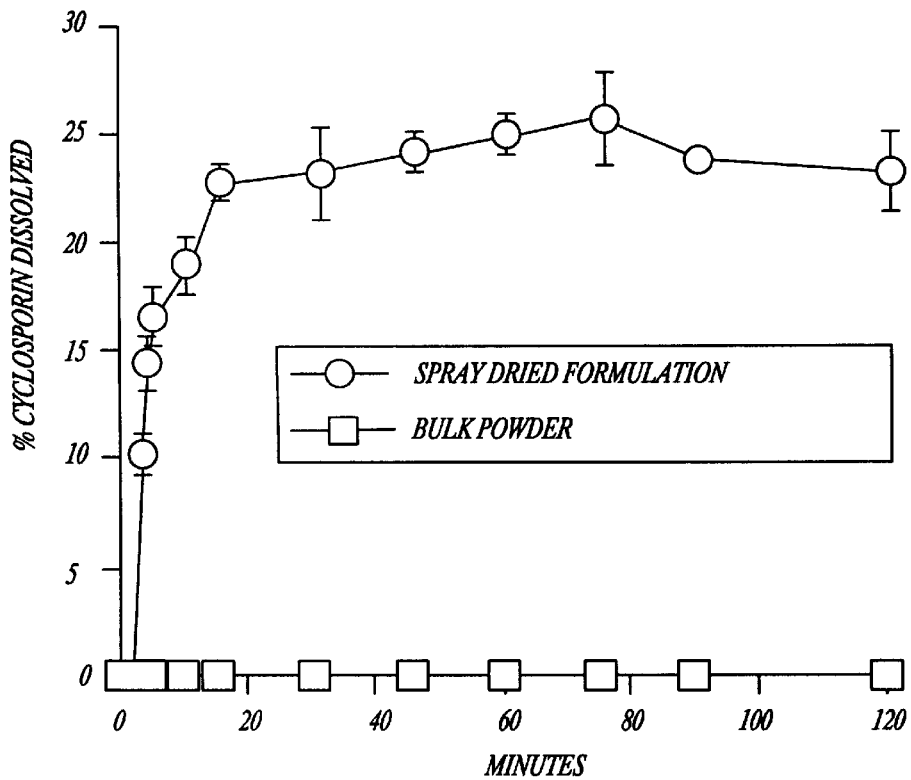
FIG. 6 is a graph comparing bulk cyclosporin powder and lecithin/gelatin coated cyclosporin prepared by spray-drying onto Nu-Pareils®.
Figure 7:
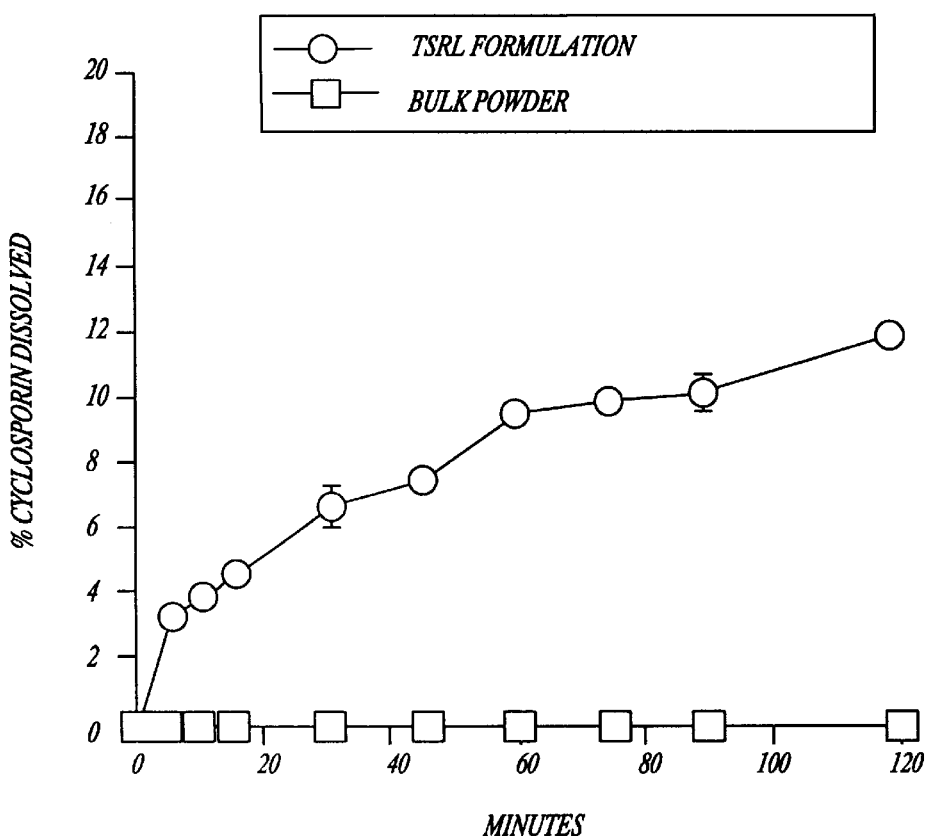
FIG. 7 is a graph showing percent cyclosporin dissolved comparing a lecithin/gelatin coated formulation according to the present invention with bulk cyclosporin powder in simulated intestinal fluid (SIF), USP, pH 7.5 @ 37° C.

Referring to FIG. 6, the dissolution of cyclosporin coated Nu-Pareils® compared with bulk cyclosporin powder. The cyclosporin coated Nu-Pareils® demonstrated both a greater initial dissolution rate and greater overall percentage dissolution over time than the bulk cyclosporin powder.

Experiments were performed in order to ascertain in vitro data regarding the performance of the subject invention. Cyclosporin, a immunosuppressive drug, has an aqueous solubility of about 0.006mg/ml. This compound was formulated with lecithin and gelatin, as described above, and its dissolution into 0.25% sodium lauryl sulfate was measured as shown in FIG. 2. The lecithin/gelatin formulation and the bulk powder form were treated in Simulated Intestinal Fluid, USP for two hours with 0.25% w/v sodium lauryl sulfate to simulate dissolution in the small intestine.

As shown in FIGS. 3 and 8, in the simulated intestinal fluid, the amount dissolved of the lecithin/gelatin coated formulation was much greater than bulk powder which was essentially insoluble over the cause of the experiment.

Experiments were performed in order to ascertain the in vivo performance of the subject invention. Cyclosporin was administered to dogs both as the bulk powder and formulated with lecithin and gelatin as described above. The lecithin/gelatin formula was prepared by dissolving one gm each of gelatin, USP/NF and lecithin NF in 100 ml of water. 0.5 gm of cyclosporin was added to this liquid and mixed on an electric stir plate at room temperature for two hours to coat the particles. The suspension was then placed on a freeze-drier and the moisture was removed by lyophylization. The lecithin/gelatin formulation and bulk powder were suspended in 10 ml of water administered via a gastric tube followed by 40 ml of water to rinse out the tube. Plasma samples were taken at 0, 15, 30, 60, 90, 120, 180, 240 and 360 minutes and assayed for cyclosporin content. FIG. 5 shows the results of this study [Abdallah et al., 1991; Bowers, 1990]. Based on these results, the lecithin/gelatin formulation showed a 2.0-fold increase in bioavailability relative to the bulk powder.

The results of the above studies demonstrate that the lecithin/gelatin coating of the present invention greatly increases both the initial dissolution rate and total percentage dissolution of previously poorly water-soluble pharmaceutical ingredients. That is, the method of coating a poorly water-soluble pharmaceutical ingredient with a pharmaceutical excipient or coating formulation which includes lecithin and gelatin greatly increased both the initial dissolution rate and overall percent dissolution of the previously poorly water-soluble pharmaceutical ingredient. The increased dissolution of the pharmaceutical ingredients treated according to the present invention allows drugs which may have poor water-solubility to be utilized since the method and coating of the present invention greatly increases the dissolution rate of these poorly water-soluble pharmaceuticals contained therein.

Pharmaceutical ingredients prepared according to the method of the present invention can be formed into tablets or loaded into capsules by methods well known to those skilled in the art without losing their enhanced dissolution rate in aqueous solution. The present invention has been shown to function in vitro as well as in vivo. The present invention increases the dissolution rate of poorly water-soluble pharmaceutical ingredients without solubilizing and/or then recrystalizing the pharmaceutical ingredient thereby eliminating the necessity for recharacterization or reidentification the pharmaceutical ingredient as discussed above for a prior art method. Since the present invention utilizes a totally aqueous system, no organic solvents are used in the process thereby eliminating the physical and environmental hazards and greatly increased costs associated therewith.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

TABLES

TABLE 1

| Range of lecithin and gelatin (% weight of final powder) = 1% to 40% (w/w). | |
|---|---|
| Material | Range of Conc. in Coating Solution (% w/v) |
| lecithin | 0.01–2.0 |
| gelatin | 0.01–2.0 |
| drug | 0.1–12 |

TABLE 2

Relative Bioavailability in Dogs of Cyclosporin Given Oral Comparing the Lecithin/Gelatin formulation with the Bulk Powder

| Formulation | $AUC_{0-6}$ ($\mu$g-hr/ml) | Relative Increase in Bioavailability |
|---|---|---|
| cyclosporin bulk powder | 0.7 | 1.0 |
| lecithin/gelatin cyclosporin formulation | 1.4 | 2.0 |

TABLE 3

Examples of Currently Marketed Water Insoluble Drugs

| Formulation | Solubility (mg/ml) | Dose (mg) | $V_{DISSOLUTION}$ (liters) |
|---|---|---|---|
| Cyclosporin[11] | 0.006 | 750 | 125 |
| Griseofulvin[12] | 0.017 | 500 | 29.4 |
| Digoxin[13] | 0.024 | 0.50 | 0.021 |
| Nifedipine[14] | 0.010 | 30.0 | 3.0 |
| Itraconozole[15] | 0.001 | 200 | 9.9 |
| Carbamazepine[16] | 0.400 | 200 | 4.3 |

TABLE 3-continued

Examples of Currently Marketed Water Insoluble Drugs

| Formulation | Solubility (mg/ml) | Dose (mg) | $V_{DISSOLUTION}$ (liters) |
|---|---|---|---|
| Piroxicam[13] | 0.010 | 20.0 | 8.2 |
| Fluconazole[13] | 0.100 | 200 | 2.0 |
| Finasteride[13] | 0.001 | 5.00 | 5.0 |
| Diflunisal[13] | 0.010 | 1000 | 3.6 |

[11] J.-P. Reymond, J.-L. Steimer, and W. Niederberger, J. Pharmacokinet, Biophar., 16:331–353 (1988).
[12] Katchen, B. Symchowicz, S., J. Pharm. Sci., 56:1108 (1967). note: solubility was measured at 39° C.
[13] J. B. Dressman, D. Fleisher, Mixing-tank Model for Predicting Dissolution Rate Control of Oral Absorption, J. Pharm. Sci., 75:109–116 (1986).
[14] D. R. Swanson, et al, Nifedipine Gastrointestinal Therapeutic System. Amer J of Med, 83:3–9 (1987).
[15] The Merek Index, Eleventh Edition, Merck & Co., Inc., Rahway, N.J., 1989.
[16] J. R. Crison, Estimating the Dissolution and Absorption of Water Insoluble Drugs in the Small Intestine, Ph.D. Thesis, The University of Michigan, 1993.

REFERENCES CITED

Abdallah and Mayersohn, "The Preparation and Evaluation of a Tablet Dosage Form of Cyclosporin in Dogs", *Pharm. Res.* 8:518–522 (1991).

Amidon et al., "A Theoretical Basis for a Biopharmaceutic Drug Classification:" The Correlation on In Vitro Drug Product Dissolution and In Vivo Bioavailability" *Pharm Res,* , 12:413–420 (1995).

Avis, "Parenteral Preparations" *Remington's Pharmaceutical Sciences,* Mack Publishing Company 15th edition, pp. 1483–1485 (1975)

Bowers, "Cyclosporin Analysis by High-Performance Liquid Chromatography: Precision, Accuracy, and Minimum Detectable Quantity", 22:11501154 (1990).

Crison, "Estimating the Dissolution and Absorption of Water Insoluble Drugs in the Small Intestine, Ph.D. Thesis, The University of Michigan (1993).

Crison and Amidon, in *Bio-International 2, Bioavailability. "Bioeguivalence and Pharmacokinetic Studies* "Expected Variation In Bioavailability for Water Insoluble Drugs" H. H. Blume and K. K. Midha, Editors, Medpharm Scientific Publishers, Stuttgart (1995).

Dressman and Fleisher, "Mixing-tank Model for Predicting Dissolution Rate control of Oral Absorption, *J. Pharm. Sci.,* 75:109–116 (1986).

Grant and Higuchi, in *Techniques of Chemistry,* "Solubility Behaviour of Organic Compounds", Volume 21, W. H. Saunders, Editor, John Wiley & Sons, Toronto, Canada (1990).

Jones, "Fluidized Bed Processing and Drying" *Int. Soc. of Pharm. Eng.,* pp 1–7 (1991)

Katchen and Symchowicz, J. Pharm. Sci., 56:11208 (1967).

Merck Index, Eleventh Edition, Merck & Co., Inc., Rahway, N.J. (1989)

Oh et al, "Estimating the Fraction Dose Absorbed from Suspensions of Poorly Soluble Compounds in Humans: A Mathematical Model. *Pharm Res,* 10:264–270 (1993)

Reymond et al., J. Pharmacokinet. Biophar., 16:331–353 (1988).

Swanson et al., "Nifedipine Gastrointestinal Therapeutic System, *Amer. J of Med.,* 83:3–9 (1987).

We claim:

1. A pharmaceutical composition comprising a pharmaceutical ingredient coated with a coating made by the method of contacting at least one pharmaceutical ingredient with a mixture consisting essentially of gelatin in a range of 0.01% (w/v) to 2.0% (w/v) and lecithin in a range of 0.001% (w/v) to 99.9% (w/v) in a solvent and drying the coated pharmaceutical to remove its solvent to increase the dissolution rate of water-insoluable pharmaceutical ingredients.

2. A pharmaceutical composition as set forth in claim 1, wherein said concentration of said gelatin component ranges from 0.01% (w/v) to 2.0% (w/v).

3. A pharmaceutical composition as set forth in claim 1, wherein said concentration of said lecithin component ranges from 0.01% (w/v) to 2.0% (w/v).

4. A pharmaceutical composition as set forth in claim 1, wherein said coated pharmaceutical ingredient is granulated.

5. A pharmaceutical composition as set forth in claim 1 further comprising sucrose beads coated with said coated pharmaceutical ingredient.

* * * * *